United States Patent
Johnson (10) Patent No.: US 10,941,375 B2
(45) Date of Patent: *Mar. 9, 2021

(54) FIBER SCAFFOLDS FOR ENHANCING CELL PROLIFERATION IN CELL CULTURE

(71) Applicant: NANOFIBER SOLUTIONS, LLC, Hilliard, OH (US)

(72) Inventor: Jed Johnson, London, OH (US)

(73) Assignee: NANOFIBER SOLUTIONS, LLC, Hilliard, OH (US)

( * ) Notice: Subject to any disclaimer, the term of this patent is extended or adjusted under 35 U.S.C. 154(b) by 132 days.

This patent is subject to a terminal disclaimer.

(21) Appl. No.: 16/379,499

(22) Filed: Apr. 9, 2019

(65) Prior Publication Data

US 2019/0249127 A1    Aug. 15, 2019

Related U.S. Application Data

(63) Continuation of application No. 13/971,154, filed on Aug. 20, 2013, now Pat. No. 10,294,449.

(60) Provisional application No. 61/691,611, filed on Aug. 21, 2012.

(51) Int. Cl.
| | |
|---|---|
| *D01D 5/00* | (2006.01) |
| *C12M 1/00* | (2006.01) |
| *C12N 5/0775* | (2010.01) |
| *C12N 5/00* | (2006.01) |
| *C12N 5/074* | (2010.01) |

(52) U.S. Cl.
CPC .......... *C12M 23/14* (2013.01); *C12N 5/0068* (2013.01); *C12N 5/0663* (2013.01); *C12N 5/0667* (2013.01); *C12N 5/0696* (2013.01); *C12N 2513/00* (2013.01); *C12N 2533/30* (2013.01)

(58) Field of Classification Search
None
See application file for complete search history.

(56) References Cited

U.S. PATENT DOCUMENTS

| 6,218,178 B1 | 4/2001 | Banes |
| 6,472,202 B1 | 10/2002 | Banes |
| 6,592,623 B1 | 7/2003 | Bowlin et al. |
| 7,172,765 B2 | 2/2007 | Chu et al. |
| 8,728,463 B2 | 5/2014 | Atala et al. |
| 9,334,476 B2 | 5/2016 | Arinzeh et al. |
| 9,771,557 B2 | 9/2017 | Arinzeh et al. |
| 9,877,822 B2 * | 1/2018 | Grosse ................. C12M 25/14 |
| 10,562,225 B2 | 2/2020 | Johnson |
| 2002/0090725 A1 | 7/2002 | Simpson et al. |
| 2002/0142458 A1 | 10/2002 | Williams et al. |
| 2004/0037813 A1 | 2/2004 | Simpson et al. |
| 2005/0047971 A1 | 3/2005 | Clements et al. |
| 2006/0128012 A1 | 6/2006 | Arinzeh et al. |
| 2007/0218118 A1 | 9/2007 | Michal et al. |
| 2008/0153163 A1 | 6/2008 | Mao et al. |
| 2009/0074832 A1 | 3/2009 | Zussman et al. |
| 2009/0208577 A1 | 8/2009 | Xu et al. |
| 2010/0273258 A1 | 10/2010 | Lannutti et al. |
| 2010/0311614 A1 | 12/2010 | Montagu et al. |
| 2012/0129713 A1 | 5/2012 | Montagu et al. |
| 2013/0052254 A1 | 2/2013 | Arinzeh et al. |
| 2013/0095165 A1 | 4/2013 | Olson et al. |
| 2013/0245784 A1 | 9/2013 | Tan et al. |
| 2013/0338791 A1 | 12/2013 | McCullen et al. |
| 2014/0079759 A1 | 3/2014 | Patel et al. |
| 2014/0107803 A1 | 4/2014 | Grosse |
| 2014/0193374 A1 | 7/2014 | Zhao et al. |
| 2015/0010607 A1 | 1/2015 | Francis et al. |
| 2015/0110846 A1 | 4/2015 | Yu et al. |
| 2016/0022873 A1 | 1/2016 | Besner et al. |
| 2016/0024690 A1 | 1/2016 | Francis et al. |
| 2016/0143745 A1 | 5/2016 | Kandel et al. |

FOREIGN PATENT DOCUMENTS

| AU | 2009207489 B2 | 9/2014 |
| CN | 102908677 A | 2/2013 |
| JP | 20115009786 A | 3/2011 |
| JP | 2012505320 A | 3/2012 |
| JP | 2013031595 A | 2/2013 |
| WO | 2006138552 A2 | 12/2006 |
| WO | 2008137659 A1 | 11/2008 |
| WO | 2009089035 A1 | 7/2009 |
| WO | 2011142667 A1 | 11/2011 |
| WO | 2014031721 A1 | 2/2014 |

OTHER PUBLICATIONS

Arteriocyte et al., Seattle 2012, 18th ISCT Annual Meeting, Jun. 5-8, 2012, 1-44, International Society for Cellular Therapy.

Carlberg et al. "Electrospun polyurethane scaffolds for proliferation and neuronal differentiation of human embryonic stem cells" (2009) Biomedical Materials 4:1-7.

Chua et al. "Surface-aminated electrospun nanofibers enhance adhesion and expansion of human umbilical cord blood hematopoietic stem/progenitor cells" (2006) Biomaterials 27:6043-6051.

Compass Biomedical product information, Adhere-34™ Culture Bag, retrieved from the internet: www.veritask.co.jp/attached/4980/Adhere-34_ENG-Manuai.pdf (Apr. 22, 2015) 1 page.

Goncharova et al. "Assays for in vitro monitoring of human airway smooth muscle (ASM) and human pulmonary arterial vascular smooth muscle (VSM) cell migration" (2006) Nature Protocols 1(6):2933-2939.

(Continued)

Primary Examiner — Scott Long
Assistant Examiner — Evelyn Y Pyla
(74) Attorney, Agent, or Firm — Troutman Pepper Hamilton Sanders LLP (57) ABSTRACT

A substrate for culturing cells that includes at least one fiber scaffold adapted to be contained within a disposable or non-disposable bioreactor, wherein the fiber scaffold further includes polymer fibers that have been created by electrospinning, and wherein the orientation of the fibers in the scaffold relative to one another is generally parallel, random, or both.

14 Claims, 11 Drawing Sheets

(56) References Cited

OTHER PUBLICATIONS

International Search Report and Written Opinion for PCT/US2013/055941 dated Nov. 12, 2013.
Kazemnejad et al. "Biochemical and Molecular Characterization of Hepatocyte-Like Cells Derived from Human Bone Marrow Mesenchymal Stem Cells on a Novel Three-Dimensional Biocompatible Nanofibrous Scaffold" (Feb. 1, 2009) J. Gastronenter. Hepatol. 24(2):278-287.
Li et al. "A three-dimensional nanofibrous scaffold for cartilage tissue engineering using human mesenchymal stem cells" (Feb. 2005) Biomaterials 26(6):599-609.
Li et al. "Human Cord Cell Hematopoiesis in Three-Dimensional Nonwoven Fibrous Matrices: In Vitro Simulation of the Marrow Microenvironment" 2001, J. Hemat. Stem Cell Res. 10:355-368.
LifeTechnologies Technical Resources: HBSS, retrieved from the Internet: www.lifetechnologies.com.
Mortera-Blanco et al. "Long-Term Cytokine-Free Expansion of Cord Blood Mononuclear Cells in Three-Dimensional Scaffolds" 2011 Biomaterials 32:9263-9270.
Nanex™ Technology Overview, retrieved from the internet: www.cellsystemsbiology.com/products_compassionbiomedical <http://www.cellsystemsbiology.com/products_compassionbiomedical> (Jun. 16, 2018) 4 pages.
Nanex™ Technology Overview, retrieved from the internet: www.compassbiomed.com/nanextrade-overview.html (Apr. 22, 2015) 1 page.
PRNewswire, retrieved from the internet: www.prnewswire.com/news-releases/arteriocyte-announces-launch-of-compass-biomedical-209935561.html (Jun. 3, 2013) 2 pages.
TaylorScientific Product Information, retrieved from the Internet: www.taylorscientific.com/taylorscientific/Tissue-Culture-Plate_Sterlie-24-Well.
Yoo et al. "Surface-Functionalized Electrospun Nanofibers for Tissue Engineering and Drug Delivery" Jan. 2009, Advanced Drug Deiivery Reviews 61:1033-1042.
Kim et al. "Evaluations of Chitosan/Poly(D,L-lactic-co-glycolic acid) Composite Fibrous Scaffold for Tissue Engineering Application" 2013, Macromolecular Res. 21:931-939.
Zhu et al. "Characterization of a co-electrospun scaffold of HLC/CS/PLA for vascular tissue engineering" 2014, Biio-Medical Mat. Engin. 24(6):1999-2005.
Lee et al. "Increased Mechanical Properties of Alligned and Isotropic Electrospun PVA Nanofiber Webs by Cellulose Nanowhisker Reinforcement" 2012, Macromolecular Research 20(1):76-83.
Herrera et al. "Randomly Oriented and Aligned Cellulose Fibres Reinforced with Cellulose Nanowhiskers, Prepared by Electrospinning" 2011, Plastics, Rubber and Composites 40(2):57-64.

* cited by examiner

FIBER SCAFFOLDS FOR ENHANCING CELL PROLIFERATION IN CELL CULTURE

This application is a continuation of U.S. patent application Ser. No. 13/971,154, filed Aug. 20, 2014, entitled "Fiber Scaffolds for Enhancing Cell Proliferation in Cell Culture," which claims priority to and benefit of U.S. Provisional Patent Application No. 61/691,611, filed Aug. 21, 2012, entitled "Fiber Scaffolds for Enhancing Cell Proliferation in Cell Culture," the entire contents of each of which is incorporated herein by reference.

BACKGROUND OF THE INVENTION

The described invention relates in general to systems and devices for use in cell culture, and more specifically to a cell culture system and substrate that includes one or more polymer scaffolds adapted to be contained within a bioreactor, wherein the fiber scaffolds further include polymer fibers that have been created by electrospinning, and wherein the orientation of the fibers in the scaffold relative to one another is generally parallel, random, or both.

Certain types of mammalian cells require attachment to a substrate so that they may adequately proliferate and undergo normal cellular function. These cells typically include a variety of stem or progenitor cells such as, for example, mesenchymal stem cells (MSC), and are of interest for a variety of clinical applications and therapies. However, the number of viable cells required for a typical therapeutic dose can be millions or billions per patient. Additionally, stem cells easily differentiate into other undesirable cell types while being expanded in vitro, thereby reducing the efficiency of the expansion process and creating a major problem for stem cell suppliers. Accordingly, there is a significant need for commercially available technologies that are capable of greatly expanding a relatively small number of stem or progenitor cells into a much larger population of such cells while maintaining the pluripotency thereof.

Current commercially used cell expansion processes typically involve large reusable stainless steel or glass bioreactors that must be cleaned and disinfected between batches or disposable, single-use bioreactors that resemble plastic bags. Stem cells are added to these bioreactors with appropriate media and reagents for promoting cell growth and then the bioreactors are closely monitored until a desired concentration of cells is achieved. For adherent cells, porous beads made from polystyrene and other polymers are added into the growth media and cell mixture to allow the cells to attach and grow normally. However, once the desired concentration of cells is achieved it is very difficult to remove all of the cells from the porous beads. This results in a low efficiency of usable cells for the desired end application. Therefore, there is an ongoing need for a cell culture system that permits desired cell growth and proliferation and that allows cultured cells to be harvested efficiently and in large numbers.

SUMMARY OF THE INVENTION

The following provides a summary of certain exemplary embodiments of the present invention. This summary is not an extensive overview and is not intended to identify key or critical aspects or elements of the present invention or to delineate its scope.

In accordance with one aspect of the present invention, a substrate for culturing cells is provided. This substrate includes at least one fiber scaffold adapted to be contained within a bioreactor. The fiber scaffold further includes polymer fibers that have been created by electrospinning and the orientation of the fibers in the scaffold relative to one another is generally parallel, random, or both.

In accordance with another aspect of the present invention, a system for culturing cells is provided. This system includes at least one fiber scaffold adapted to be contained within a bioreactor, and a bioreactor. The fiber scaffold further includes polymer fibers that have been created by electrospinning and the orientation of the fibers in the scaffold relative to one another is generally parallel, random, or both. The bioreactor may be disposable or permanent (i.e., reusable).

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

BRIEF DESCRIPTION OF THE DRAWINGS

The accompanying Figures, which are incorporated into and form a part of the specification, illustrate one or more exemplary embodiments of the invention and, together with the general description given above and detailed description given below, serve to explain the principles of the invention, and wherein.

DETAILED DESCRIPTION OF THE INVENTION

Exemplary embodiments of the present invention are now described with reference to the Figures. Although the following detailed description contains many specifics for the purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention. With general reference to FIGS. 1-15, one or more specific embodiments of this invention shall now be described in greater detail.

In accordance with this invention, the process of electrospinning is driven by the application of a high voltage, typically between 0 and 30 kV, to a droplet of a polymer solution or melt at a flow rate between 0 and 50 ml/h to create a condition of charge separation between two electrodes and within the polymer solution to produce a polymer jet. A typical polymer solution includes a polymer such as polycaprolactone, polystyrene, or polyethersulfone and a solvent such as 1,1,1,3,3,3-Hexafluoro-2-propanol, N,N-Dimethylformamide, acetone, or tetrahydrofuran in a concentration range of 1-50 wt %. As the jet of polymer solution travels toward the electrode it is elongated into small diameter fibers typically in the range of 0.1-30 μm.

In preparing an exemplary scaffold, a polymer nanofiber precursor solution is prepared by dissolving 9 wt % polyethylene terephthalate (PET) (Indorama Ventures) in a mixture of nine parts 1,1,1,3,3,3-hexafluoroisopropanol (HFIP) and one part trifluoroacetic acid. The solution is heated to 60° C. followed by continuous stirring to dissolve the PET. The solution is cooled to room temperature and placed in a syringe (e.g., 60 cc) with a blunt tip needle (e.g., 20 gauge). The nanofibers are formed by electrospinning using a high voltage DC power supply (Glassman High Voltage, Inc., High Bridge, N.J.) set to 1 kV-40 kV (e.g., +15 kV) positive or negative polarity, a 5-30 cm (e.g., 15 cm) tip-to-substrate distance, and a 1 μl/hr to 100 mL/hr (e.g., 10 ml/hr) flow rate. It is possible to use a needle array including a large number of needles (e.g., >1000) to increase system output. The scaffold may be placed in a vacuum overnight and heated to ensure removal of residual solvent (typically less than 10 ppm) and treated using radio frequency gas plasma or corona for one second to one minute to make the fibers more hydrophilic and promote cell attachment thereto.

In accordance with this invention, it is possible to produce nanometer or micrometer sized fibers from a variety of synthetic and natural polymers. Suitable synthetic polymers include polycaprolactone (PCL), polyethylene terephthalate (PET), polystyrene (PS), polylactic acid (PLA), polyglycolic acid (PGA), polyurethane (PU), polyethersulfone, polyamide, Eudragit® (a polymerization of acrylic and methacrylic acids or their esters), polyetherketoneketone (PEKK), polyglycerol sebacate (PGS), polyhydroxybutyrate (PHB), trimethylene carbonate (TMC) and/or combinations thereof and/or derivatives thereof. Suitable natural polymers include gelatin, collagen, chitosan, fibrinogen, hyaluronic acid, cellulose, and/or combinations thereof and/or derivatives thereof. Suitable solvents may include acetone, dimethylformamide, trifluoroacetic acid, hexafluoroisopropanol, acetic acid, dimethylacetamide, chloroform, dichloromethane, water, ionic compounds, or combinations thereof. By predetermining the optimum fiber material and fiber diameter for each cell type or application, higher rates of cellular expansion, while maintaining a larger percentage of pluripotent cells, can be achieved as compared to other technologies.

The polymer fibers of this invention may include non-resorbable materials such as polyethylene, terephthalate, silicone, polyurethane, polycarbonate, polyether-ketoneketone, polyethersulfone, polyamide, polystyrene, Eudragit®, polyethylene terephthalate, polypropylene, or combinations thereof. and/or resorbable materials such as polycaprolactone (PCL), polylactic acid (PLA), polyglycolic acid (PGA), polyethylene terephthalate (PET) polypropylene (PP), or combinations thereof, and/or materials that may be preferentially dissolved by changes in pH, temperature or the addition of reagents to facilitate cell harvesting. Eudragit® is a pH sensitive polymer and Poly(N-isopropylacrylamide) is a thermo-responsive polymer that facilitates cell release from the fibers. The polymer fibers may be coated or otherwise treated with at least one compound that is operative to promote cellular attachment to the scaffold or to prohibit unwanted cell differentiation, and those compounds may include proteins, peptides, cytokines, small molecules (e.g., drugs) or combinations thereof. The polymer fibers of this invention may also include a core/shell construction which may be coated with a compound that promotes cell release therefrom.

The fiber scaffolds of the present invention may be used with bioreactors of different sizes and shapes, as well as those that are disposable or permanent (i.e., reusable). For the purpose of incorporating the fiber scaffolds of this invention into such bioreactors while still facilitating easy cell removal, fiber scaffolds of various sizes, shapes, and porosities may be utilized (see FIGS. 1-2). The polymer fibers in these scaffolds may be randomly arranged relative to one another or may be aligned with one another (see FIGS. 3-4). Depending on bioreactor geometry, the fiber scaffolds of this invention may be adhered to the bioreactor walls or other surfaces or may be dispersed, individual fibers that are free-floating in the cell culture media contained in a bioreactor (see FIGS. 5-6). These various fiber structures may be placed into the bioreactor at a manufacturing facility, sealed, sterilized, and then shipped to the customer. Alternately, these fiber structures may be sold separately and placed in the bioreactor by a person performing cell culture. To adhere polymer fiber to bioreactor bags, fiber is deposited directly onto the bag surface by placing a negatively charged substrate behind the bag or placing an anti-static bar behind the bag. This technique permits uniform deposition of the positively charged fibers onto the bag surface. Alternatively, the fibers may be attached to the bioreactor walls with adhesives, heat, laser welding, ultrasonic welding, or other methods.

In some embodiments of this invention, the fiber scaffold has been manufactured as a sheet of polymer fibers and then cut into pieces of at least one predetermined size prior to placement in the bioreactor. Cutting may be accomplished with scissors, a knife, or by tearing the polymer fiber sheet apart to form individual scaffolds of various sizes such as, for example, about 1 mm$^3$ fiber scaffolds to about 1 cm$^3$ fiber scaffolds. For embodiments that utilize dispersed fibers, a tissue homogenizer may be used to chop and shred polymer fiber sheets, which then allows the fibers to then be fully dispersed in liquid.

Figure 1:
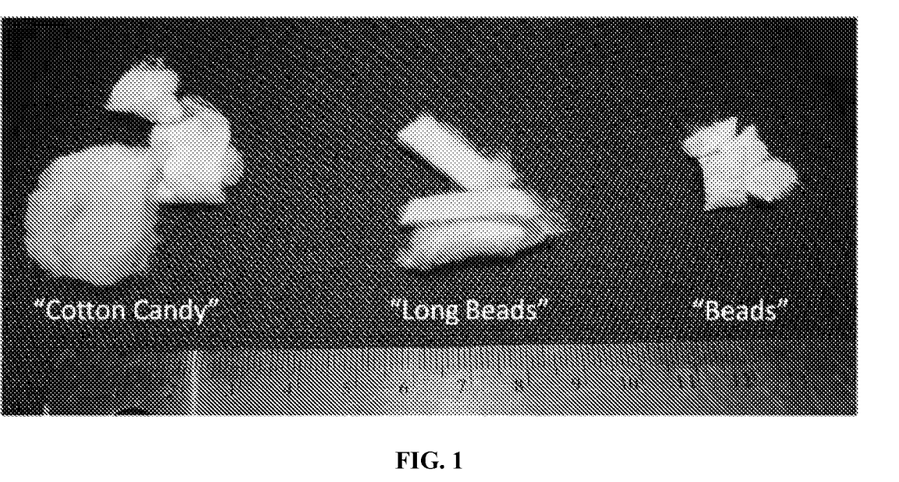
FIG. 1 is a photograph of exemplary polymer scaffolds of various shapes and sizes, in accordance with the present invention.
Figure 2:
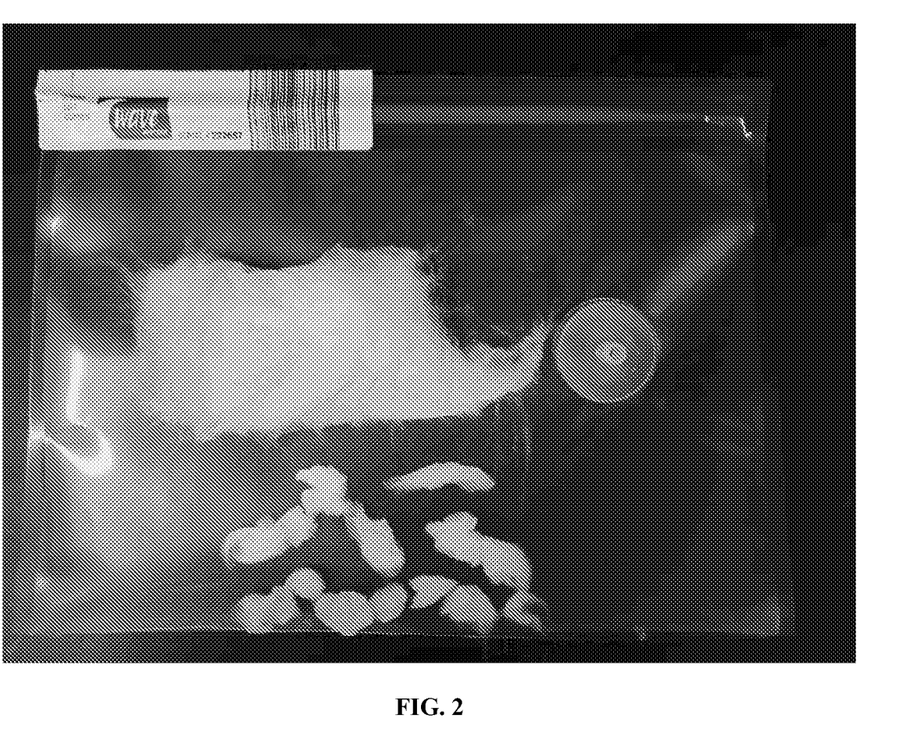
FIG. 2 is a photograph of exemplary polymer scaffolds of various shapes and sizes placed inside of a disposable bag bioreactor.
Figure 3:
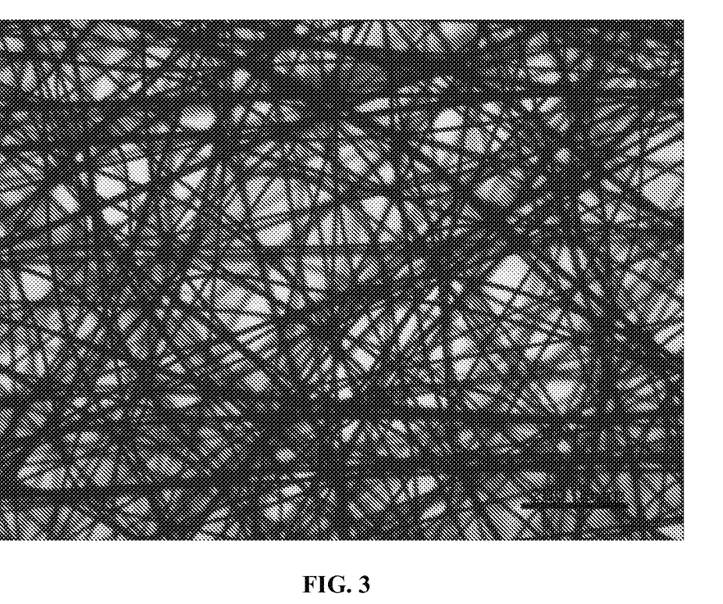
FIG. 3 is a photograph of randomly oriented polymer fibers deposited onto the surface of a disposable bag bioreactor.
Figure 4:
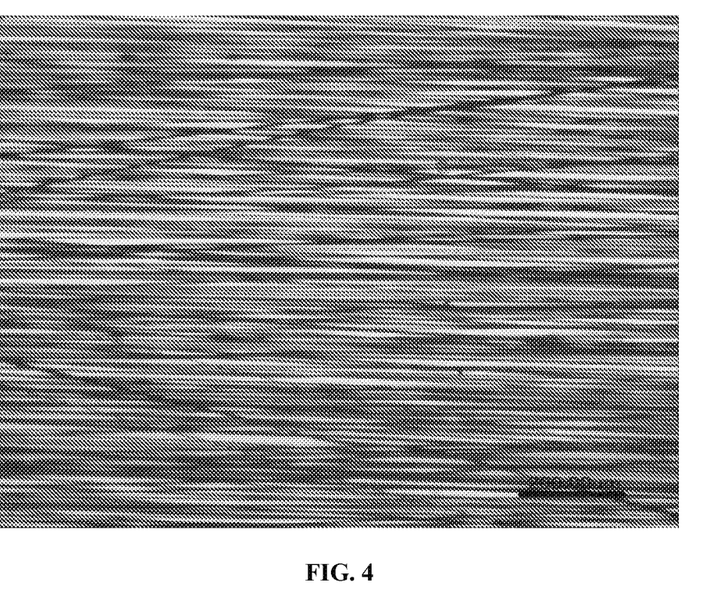
FIG. 4 is a photograph of aligned polymer fibers deposited onto the surface of a disposable bag bioreactor.
Figure 5:
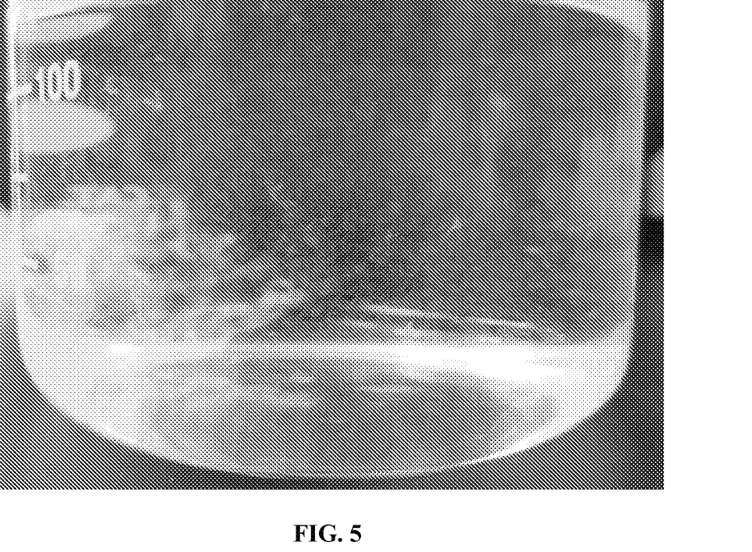
FIG. 5 is a photograph of dispersed or free-floating fibers in solution.
Figure 6:
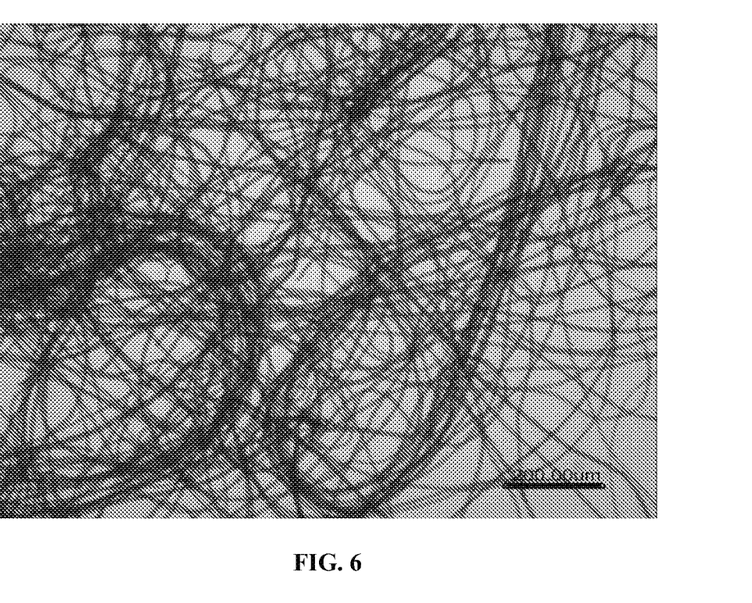
FIG. 6 is a light microscope image of dispersed polymer fiber showing significantly more spacing between fibers than when in a consolidated mat or other structure.
Figure 7:
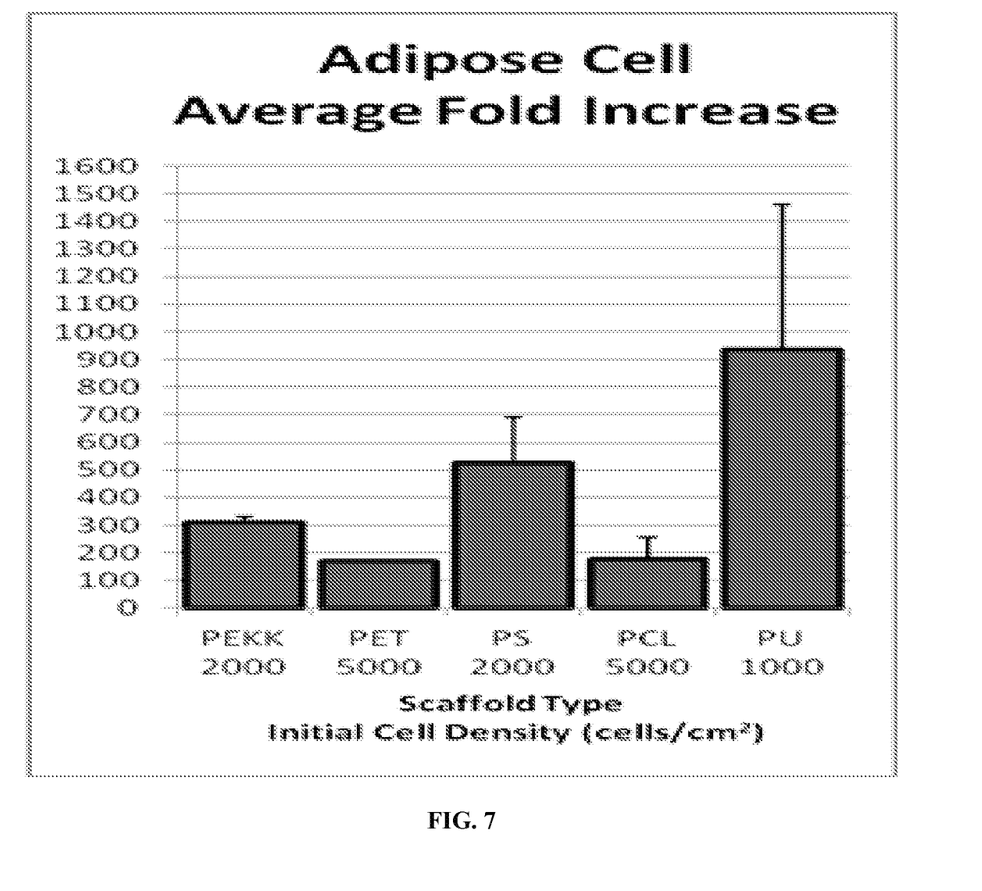
FIG. 7 is a data graph illustrating the proliferation of human adipocyte-derived stem cells on different types of nanofibers, in accordance with the present invention.

FIG. 7 is a data graph illustrating the proliferation of human adipose-derived stem cells (hADSCs) on different types of nanofibers. Multiple replicates of hADSCs were seeded in 24-well plates containing five different randomly oriented three-dimensional nanofiber matrices. Seven days after initial seeding, the cells were trypsinized and re-suspended in culture media. Cell enumeration and viability was determined by trypan blue exclusion. Fold increases of hADSCs grown on three-dimensional nanofiber matrices relative to control cells grown on standard two-dimensional tissue culture polystyrene (TCPS) are quantified in FIG. 7. The data indicates that each three-dimensional nanofiber matrix supports the growth of hADSCs and results in a significant increase in expansion rates of cells compared to two dimensional TCPS.

Figure 8:
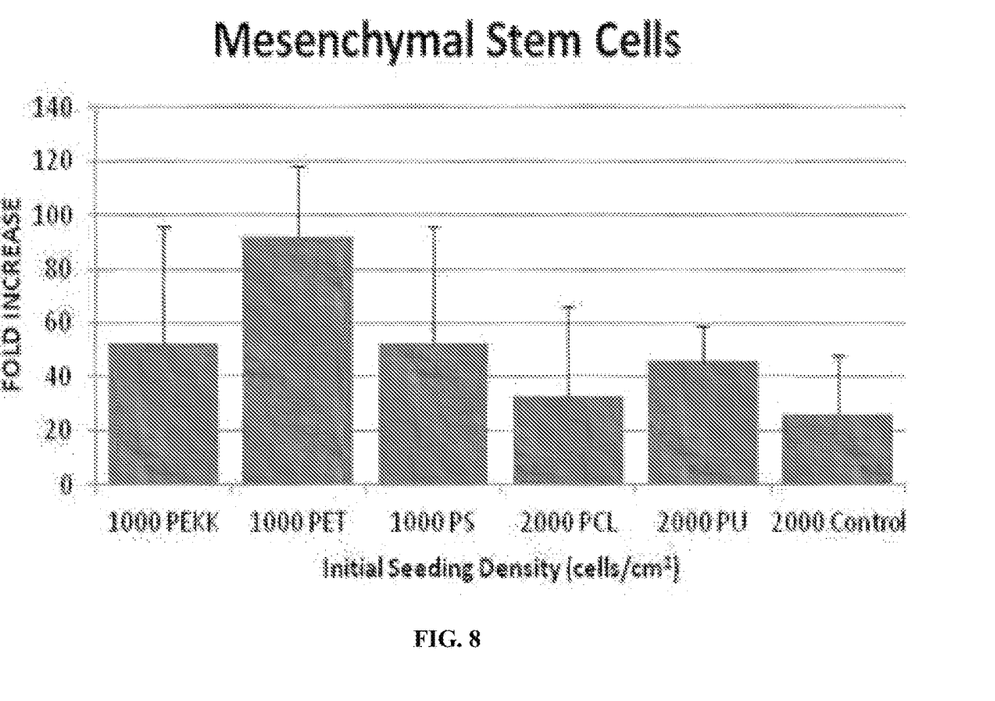
FIG. 8 is a bar graph illustrating increased cell growth/expansion on the polymer fibers of the present invention.
Figure 9:
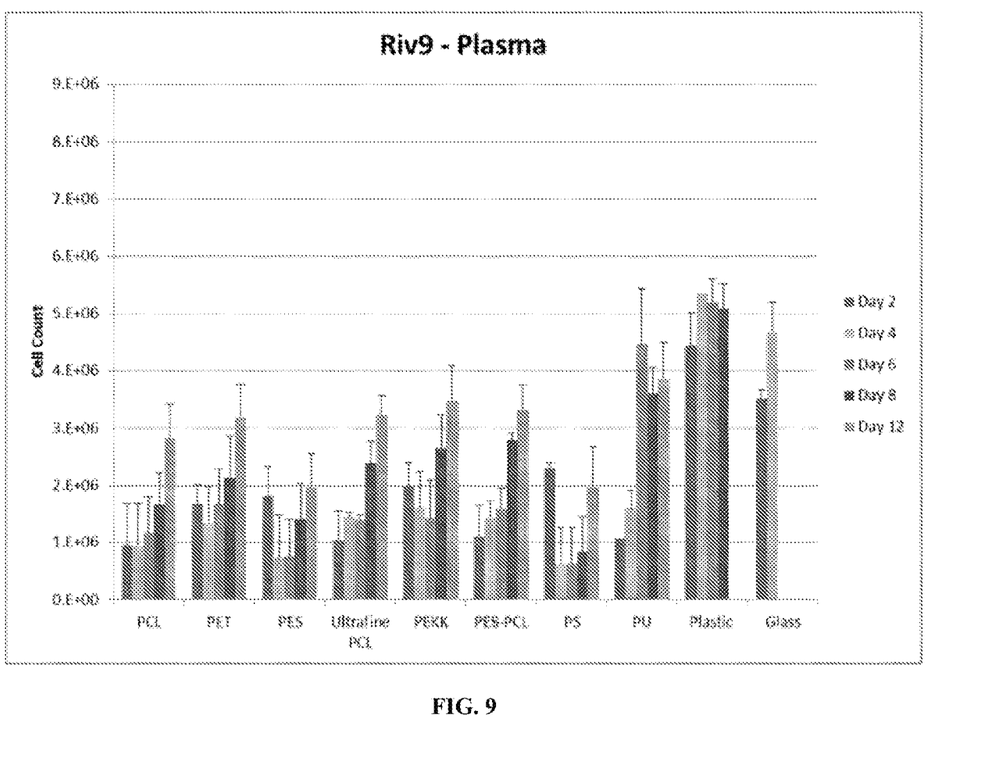
FIGS. 9-12 are bar graphs presenting human induced pluripotent stem cell (iPSs) and embryonic stem cell (ECs) data.
Figure 10:
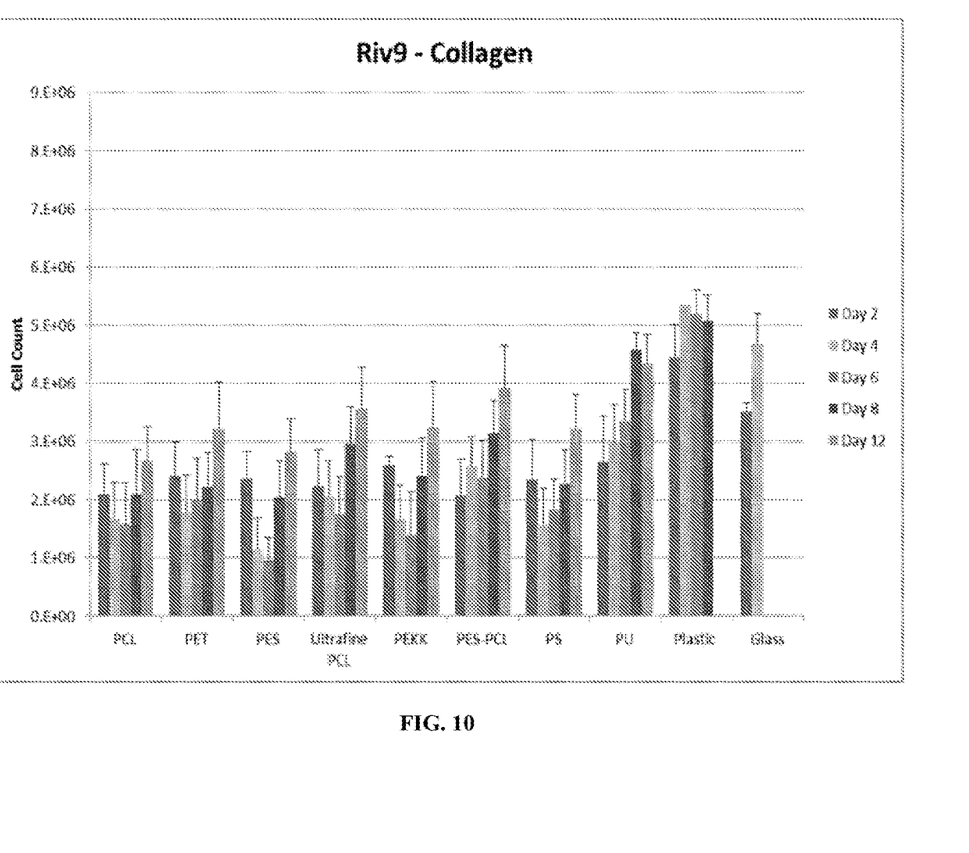
Figure 11:
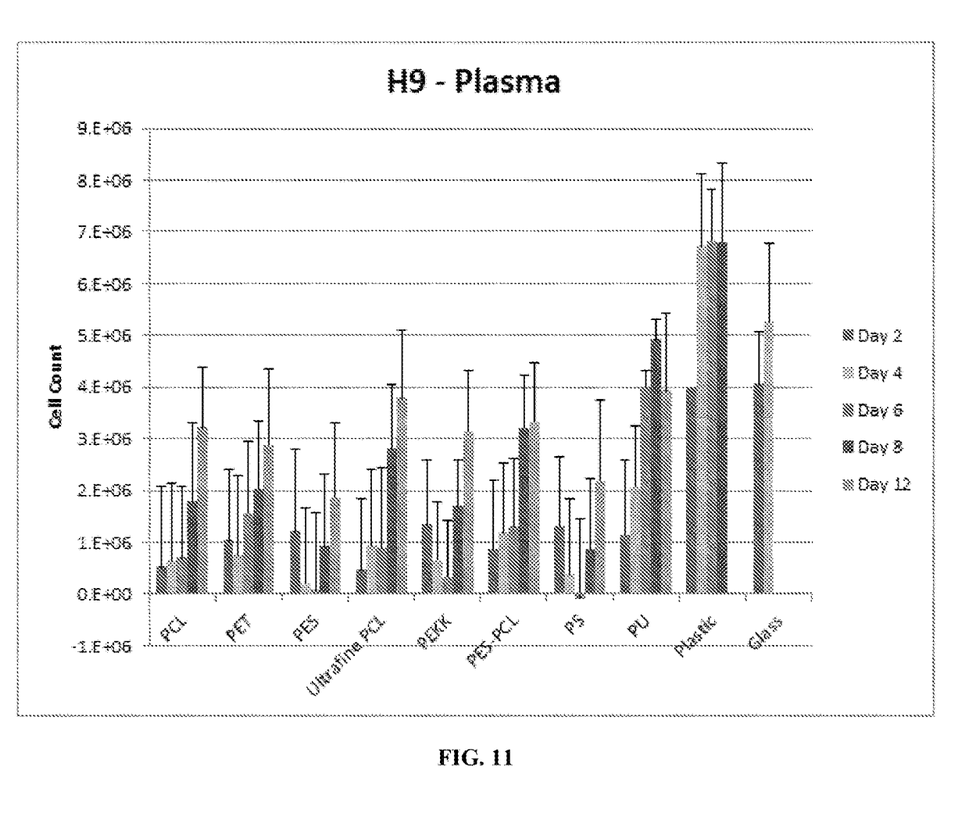
Figure 12:
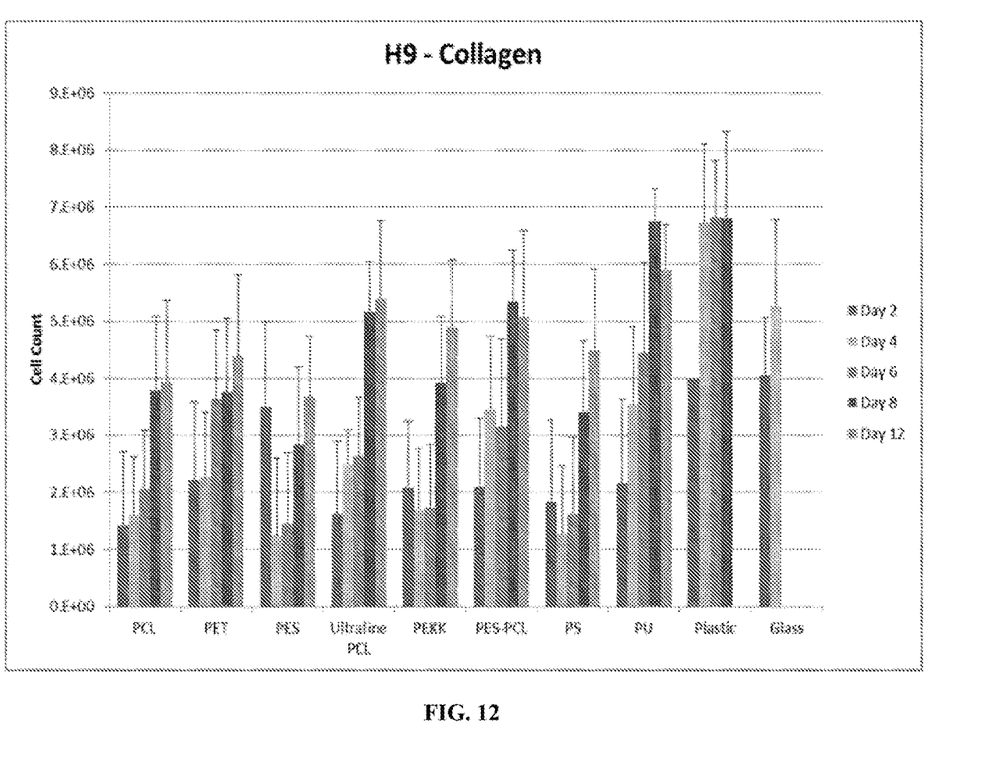

FIG. 8 is a bar graph that illustrates increased cell growth/expansion on the polymer fibers of the present invention. With regard to the data appearing in FIG. 8, multiple replicates of human mesenchymal stem cells (hMSCs) were seeded in 24-well plates containing five different randomly oriented three-dimensional fiber matrices. Seven days after initial seeding, cells were trypsinized and resuspended in culture media. Cell enumeration and viability was determined by trypan blue exclusion. Fold increases of hMSCs grown on three dimensional matrices relative to control cells grown on standard 2D tissue culture polystyrene (TCPS) are shown in FIG. 8. The data indicate that each three-dimensional fiber matrix supports the growth of hMSCs and demonstrates a significant increase in the expansion rates of cells cultured in three dimensions compared to two dimensional TCPS.

Figure 13:
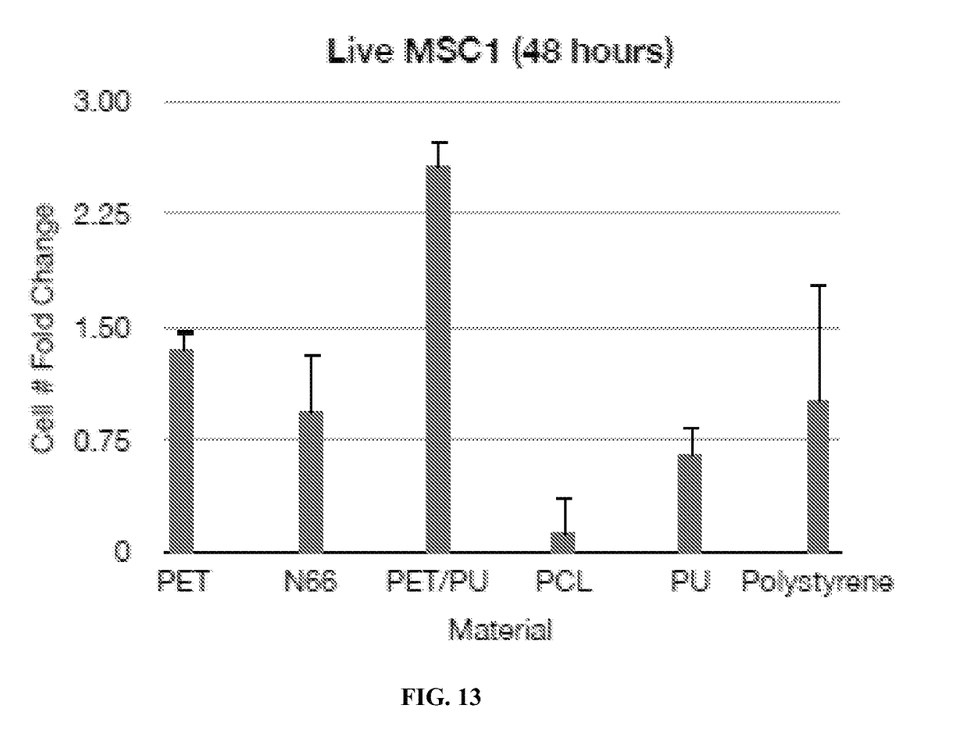
FIGS. 13-14 are bar graphs that illustrate enhanced cell growth on nanofiber scaffolds made from a blend of PET and PU compared with plain PET and plain PU using human mesenchymal stem cells.
Figure 14:
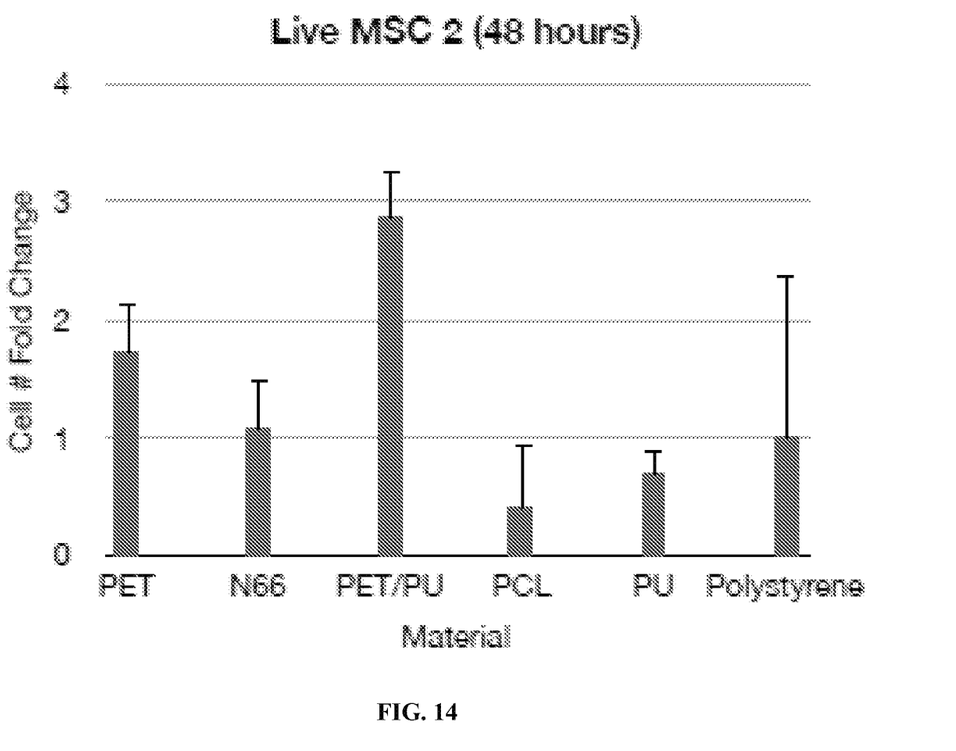
Figure 15:
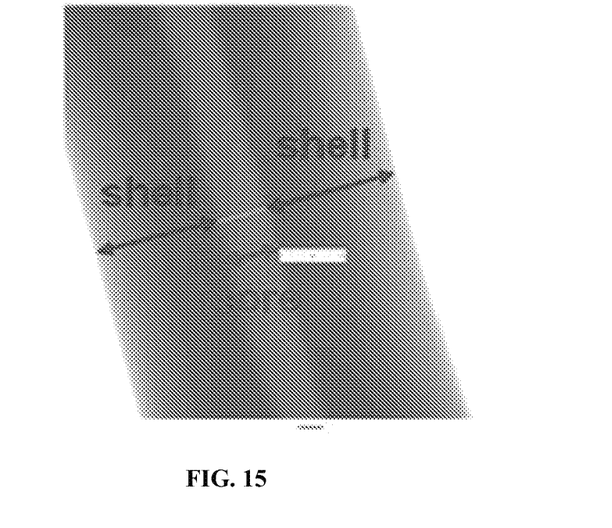
FIG. 15 is a photograph of a polymer fiber having a core/shell construction.

FIGS. 9-12 are bar graphs presenting human induced pluripotent stem cell (iPSs) and embryonic stem cell (ECs) data. Embryonic stem cells typically need feeder cells or collagen on which to grow and the data in these Figures demonstrates nearly the same growth, but using a clean synthetic fiber scaffold. This feature of the present invention is important for cost reduction and translation to clinical therapies due to the superior control of the synthetic surface. FIGS. 13-14 are bar graphs that illustrate enhanced cell growth on nanofiber scaffolds made from a blend of PET and PU compared with just PET and/or just PU using human MSCs. FIG. 15 is a photograph of a polymer fiber that is compatible with the present invention, wherein the fiber has a core/shell construction.

While the present invention has been illustrated by the description of exemplary embodiments thereof, and while the embodiments have been described in certain detail, it is not the intention of the Applicant to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the applicant's general inventive concept.

What is claimed:

1. A fiber scaffold comprising electrospun polymer fibers, wherein each electrospun polymer fiber includes a blend of polyethylene terephthalate and polyurethane, the blend having a weight ratio of about 2:8 polyethylene terephthalate to polyurethane.

2. The fiber scaffold of claim 1, wherein the electrospun polymer fibers have an orientation relative to one another that is generally parallel, random, or a combination thereof.

3. The fiber scaffold of claim 1, wherein the electrospun polymer fibers have a diameter in the range of 0.1-30 μm.

4. The fiber scaffold of claim 1, formed into a sheet.

5. The fiber scaffold of claim 1, wherein the electrospun polymer fibers further comprise a treatment configured to promote cellular attachment to the fiber scaffold.

6. The fiber scaffold of claim 5, wherein the treatment is selected from the group consisting of proteins, peptides, cytokines, small molecules, and combinations thereof.

7. The fiber scaffold of claim 1, further comprising electrospun polymer fibers that include a synthetic polymer selected from the group consisting of polycaprolactone, polystyrene, polylactic acid, polyglycolic acid, polyethersulfone, polyamide, polyetherketoneketone, a polymerization of acrylic and methacrylic acids or their esters, polyglycerol sebacate, polyhydroxybutyrate, trimethyl carbonate, combinations thereof, and derivatives thereof.

8. The fiber scaffold of claim 1, further comprising electrospun polymer fibers that include a natural polymer selected from the group consisting of gelatin, collagen, fibrinogen, hyaluronic acid, cellulose, combinations thereof, and derivatives thereof.

9. The fiber scaffold of claim 1, further comprising electrospun polymer fibers that include a non-resorbable material selected from the group consisting of polyethylene, terephthalate, silicone, polycarbonate, polyether-ketoneketone, polyethersulfone, polyamide, polystyrene, a polymerization of acrylic and methacrylic acids or their esters, polypropylene, and combinations thereof.

10. The fiber scaffold of claim 1, further comprising electrospun polymer fibers that include a resorbable material selected from the group consisting of polycaprolactone, polylactic acid, polyglycolic acid, polyhydroxybutyrate, trimethylene carbonate, and combinations thereof.

11. The fiber scaffold of claim 1, wherein the electrospun polymer fibers further comprise a material that may be dissolved by one or more of a changing pH, a changing temperature, and an addition of reagents that facilitate the harvesting of cells from the fibers.

12. The fiber scaffold of claim 1, wherein the electrospun polymer fibers have a core/shell construction.

13. A system for culturing cells, the system comprising the scaffold of claim 1.

14. The system of claim 13, further comprising a bioreactor.

* * * * *